(12) United States Patent
Wendlinger et al.

(10) Patent No.: US 9,120,716 B2
(45) Date of Patent: *Sep. 1, 2015

(54) PROCESS FOR THE PREPARATION OF 2,3,3,3 TETRAFLUOROPROPENE

(75) Inventors: Laurent Wendlinger, Soucieu en Jarrest (FR); Philippe Bonnet, Lyons (FR); Anne Pigamo, Francheville (FR); Nicolas Doucet, Lyons (FR)

(73) Assignee: Arkema France, Colombes (FR)

( * ) Notice: Subject to any disclaimer, the term of this patent is extended or adjusted under 35 U.S.C. 154(b) by 132 days.

This patent is subject to a terminal disclaimer.

(21) Appl. No.: 13/879,435

(22) PCT Filed: Oct. 22, 2010

(86) PCT No.: PCT/IB2010/003028
§ 371 (c)(1),
(2), (4) Date: Jun. 24, 2013

(87) PCT Pub. No.: WO2012/052797
PCT Pub. Date: Apr. 26, 2012

(65) Prior Publication Data
US 2013/0267740 A1   Oct. 10, 2013

(51) Int. Cl.
*C07C 17/25* (2006.01)
*C07C 17/383* (2006.01)
*C07C 17/20* (2006.01)
*C07C 17/42* (2006.01)
*C07C 21/18* (2006.01)

(52) U.S. Cl.
CPC ............... *C07C 17/206* (2013.01); *C07C 17/25* (2013.01); *C07C 17/383* (2013.01); *C07C 17/42* (2013.01)

(58) Field of Classification Search
CPC ........ C07C 17/206; C07C 21/18; C07C 17/25
USPC .................................................. 570/156, 170
See application file for complete search history.

(56) References Cited

U.S. PATENT DOCUMENTS

| 5,336,816 | A  | * | 8/1994  | Achord et al. ................ 570/188 |
|-----------|----|---|---------|---------------------------------------|
| 5,714,651 | A  |   | 2/1998  | Elsheikh et al.                       |
| 7,795,480 | B2 | * | 9/2010  | Merkel et al. ................. 570/155 |
| 8,207,383 | B2 | * | 6/2012  | Deur-Bert et al. ............ 570/169  |
| 8,398,882 | B2 |   | 3/2013  | Rao et al.                            |
| 2009/0203945 | A1 | * | 8/2009 | Mukhopadhyay et al. ... 570/135 |
| 2009/0240090 | A1 |   | 9/2009 | Merkel et al.                   |
| 2009/0287026 | A1 |   | 11/2009 | Kopkalli et al.                |
| 2010/0191025 | A1 | * | 7/2010 | Perdrieux ...................... 570/155 |
| 2010/0210882 | A1 |   | 8/2010 | Sharratt et al.                 |

FOREIGN PATENT DOCUMENTS

EP           0 939 071 A1    1/1999
WO    WO 9325507 A1  * 12/1993

(Continued)

OTHER PUBLICATIONS

WO 2008149011 A2, Dec. 2008, pp. 1-4; English translation.*

*Primary Examiner* — Jafar Parsa
*Assistant Examiner* — Medhanit Bahta
(74) *Attorney, Agent, or Firm* — Brinks Gilson & Lione

(57) ABSTRACT

The present invention provides a process for preparing 2,3,3,3-tetrafluoropropene, comprising the following steps: (a) catalytic reaction of 1,1,1,2,3-pentachloropropane and/or 1,1,2,2,3-pentachloropropane with HF into product 2-chloro-3,3,3-trifluoropropene; (b) catalytic reaction of the thus-obtained 2-chloro-3,3,3-trifluoropropene into 2,3,3,3-tetrafluoropropene.

21 Claims, 4 Drawing Sheets

(56) References Cited

FOREIGN PATENT DOCUMENTS

| WO | WO 2007/079431 A2 | 7/2007 |
| WO | WO 2009/003084 A1 | 12/2008 |
| WO | WO 2008149011 A2 * | 12/2008 |
| WO | WO 2009/015317 A1 | 1/2009 |
| WO | WO 2009/118628 A1 | 10/2009 |
| WO | WO 2005/108334 A1 | 11/2009 |
| WO | WO 2011077192 A1 * | 6/2011 |

* cited by examiner

PROCESS FOR THE PREPARATION OF 2,3,3,3 TETRAFLUOROPROPENE

This application is the national phase under 35 USC §371 of prior PCT International Application Number PCT/IB2010/003028 filed Oct. 22, 2010 which designated the United States of America.

FIELD OF THE INVENTION

The present invention relates to the preparation of 2,3,3,3-tetrafluoropropene (1234yf). More particularly, the present invention relates to a two steps process wherein pentachloropropane, including 1,1,1,2,3-pentachloropropane (HCC 240db) and/or 1,1,2,2,3-pentachloropropane (HCC 240aa), is first contacted with hydrogen fluoride (HF), this first step (a) providing 2-chloro-3,3,3-trifluoropropene (HFO 1233xf), which is then converted into 1234yf in a second step (b).

The desired product, 1234yf is known to have utility as a foam blowing agent, refrigerant, aerosol propellant, heat transfer media, fire extinguisher, etc. Furthermore, 1234yf is known to have zero Ozone Depletion Potential (ODP) and very low Global Warming Potential (GWP) of much less than 150.

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes of production HFOs compounds, in particular of propenes, were developed.

US2009/0240090 discloses the gas-phase reaction of 1,1,1,2,3-pentachloropropane (HCC 240db) into product 2-chloro-3,3,3-trifluoropropene (HCFO 1233xf). Example 3 uses a catalyst comprised of fluorinated $Cr_2O_3$. The product 1233xf thus produced is then converted into product 2-chloro-1,1,1,2-tetrafluoropropane (244bb) in a liquid phase reaction. This product 244bb is then converted into the desired 1234yf.

WO2005/108334, example 3, discloses that 240db is passed through a flow reactor for a contact time for about 5 to 50 seconds at about 250-400° C. in the presence of 5 molar excess of HF over a 50 g ⅛-inch $Cr_2O_3$ catalyst bed to give 244db (2-chloro-1,1,1,3-tetrafluoropropane). It is further indicated that the 244db is then dehydrochlorinated by passing it over a $Cr_2O_3$ catalyst (50 g) at 425-550° C. with a contact time of 25 to 30 seconds to afford product 1234ze (1,3,3,3-tetrafluoropropene).

The literature is generally about a scheme involving preparation of 1234yf via the 244 route.

There is still a need for further processes for manufacturing 1234yf.

SUMMARY OF THE INVENTION

The invention is based on the finding that it is possible to prepare the compound 1234yf starting from pentachloropropane. In one embodiment, this process is conducted without preparing in an intermediate stage the product 244bb (2-chloro-1,1,1,2-tetrafluoropropane).

Hence, the invention provides a process for preparing 2,3,3,3-tetrafluoropropene, comprising the following steps:
 (a) catalytic reaction of 1,1,1,2,3-pentachloropropane and/or 1,1,2,2,3-pentachloropropane with HF into product 2-chloro-3,3,3-trifluoropropene;
 (b) catalytic reaction of the thus-obtained 2-chloro-3,3,3-trifluoropropene into 2,3,3,3-tetrafluoropropene.

Embodiments are the following:
step (b) comprises:
 (i) contacting 2-chloro-3,3,3-trifluoro-1-propene (1233xf) with hydrogen fluoride HF in gas phase in the presence of a fluorination catalyst under conditions sufficient to produce a reaction mixture;
 (ii) separating the reaction mixture into a first stream comprising HCl, 2,2,2,3-tetrafluoropropene (1234yf) and a second stream comprising HF, unreacted 2-chloro-3,3,3-trifluoro-1-propene (1233xf) and 1,1,1,2,2-pentafluoropropane (245cb);
 (iii) recycling at least a part of the second stream at least in part back to step (i).
the first stream is further separated into HCl and 2,2,2,3-tetrafluoropropene (1234yf), preferably in a distillation step.
step (b) comprises:
 (i) contacting 2-chloro-3,3,3-trifluoro-1-propene (1233xf) with hydrogen fluoride HF in gas phase in the presence of a fluorination catalyst under conditions sufficient to produce a reaction mixture;
 (ii) separating the reaction mixture into HCl and a stream containing the fluorinated products;
 (iii) separating said stream containing the fluorinated products into a first stream comprising 2,2,2,3-tetrafluoropropene (1234yf) and a second stream comprising HF, unreacted 2-chloro-3,3,3-trifluoro-1-propene (1233xf) and 1,1,1,2,2-pentafluoropropane (245cb);
 (iv) recycling at least a part of the second stream at least in part back to step (i).
step (b) is carried out in the presence of a catalyst comprising Ni—Cr, preferably supported. Said catalyst can be supported on a support selected from fluorinated alumina, fluorinated chromia, fluorinated activated carbon or graphite carbon.
step (a) is carried out in a liquid-phase.
step (a) is carried out in an organic medium.
the process is carried out in a solvent. The solvent can be selected from 1,2-dichloroethane, 1,2,3-trichloropropane, 1-chloro-1-fluoroethane, 1,1-difluoroethane, 1,1-dichloroethane and 1,3-dichloro-1-fluorobutane, tetrachlorofluoropropane isomers, trichlorodifluoropropane isomers and dichlorotrifluoropropane isomers, 1,1,1,3,3-pentafluorobutane and 1,1,2-trichloro-2,2-difluoroethane, nitrated solvents including nitromethane and nitrobenzene, sulfones including tetramethylene sulfone and dimethyl sulfone, 1,1,2-trichloro-2-fluoroethane or perchloroethylene, or mixtures thereof, preferably 1,1,2-trichloro-2,2-difluoroethane.
the catalyst is an ionic liquid.
the product of the reaction is withdrawn in the gaseous state.
the process comprises:
 (i) contacting 1,1,1,2,3-pentachloropropane or/and 1,1,2,2,3-pentachloropropane with hydrogen fluoride in a liquid phase in an organic medium under conditions sufficient to form a reaction mixture comprising 2-chloro-3,3,3-trifluoropropene;

(ii) separating the reaction mixture into a first stream comprising HCl, and a second stream comprising HF and 2-chloro-3,3,3-trifluoropropene.

step (a) is carried out in a gas-phase.

the process is carried out in presence of oxygen.

step (a) is carried out in the presence of a catalyst comprising Ni—Cr, preferably supported. Said catalyst can be supported on a support selected from fluorinated alumina, fluorinated chromia, fluorinated activated carbon or graphite carbon.

the temperature in step (b) is higher than the temperature of step (a) by at least 30° C.

the 1,1,1,2,3-pentachloropropane contains up to 40 mol % of isomer 1,1,2,2,3-pentachloropropane.

the process is continuous.

The invention relates to also the products obtained by following the steps of the process disclosed herewith, in particular a mixture containing mainly 1234yf and impurities and/or unreacted starting materials and/or co-products.

DETAILED DESCRIPTION OF EMBODIMENTS

Figure 1:
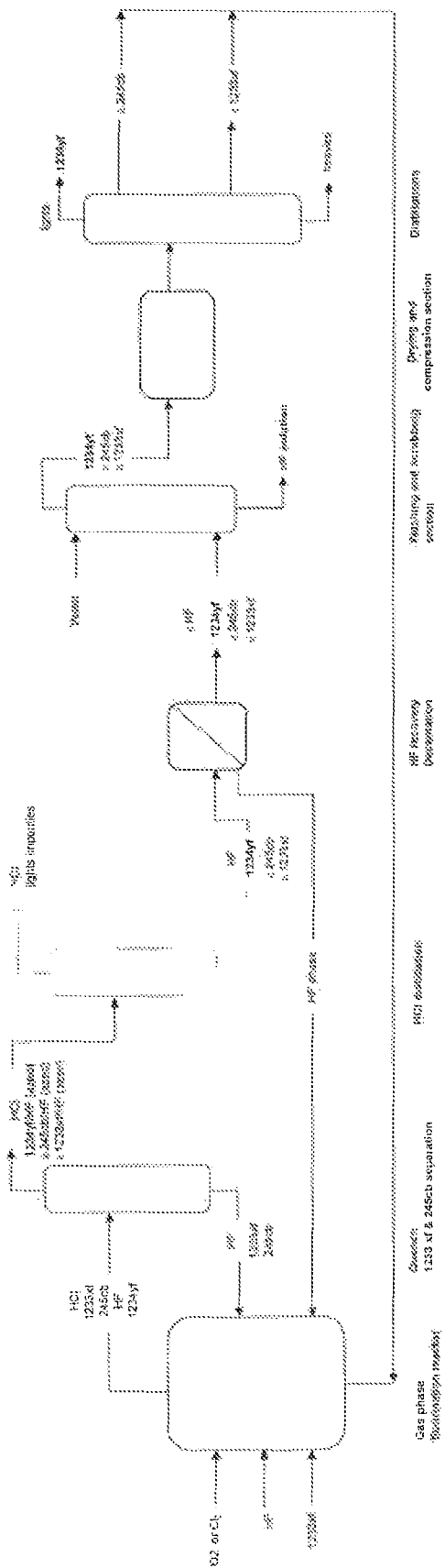
FIG. 1 is a schematic representation of a process implementing step (b)

Gas-Phase Reaction of 1233xf into 1234yf.

The second stage of the method of preparation of the 1234yf is a fluorination reaction of the 2-chloro-3,3,3-trifluoro-1-propene (1233xf) obtained at the previous stage in 2,3,3,3-tetrafluoro-1-propene, the desired product.

The two stages can be implemented continuously or in a discontinuous way, with intermediate storage of the 1233xf.

This second stage can comprise direct fluorination in the presence of HF, on a catalyst, in gas phase.

This gas phase reaction is carried out in the presence of a fluorination catalyst. The reaction is carried out in a single gas-phase reactor. The temperatures, pressures and contact times are easily determined by the skilled worker. Typical conditions are given below.

The level of the conversion and selectivity of the desired product can vary according to the processing conditions. The catalyst can be present in any suitable form, such as fixed or fluidized bed, preferably in a fixed bed. The direction of flow may be downward or upward.

This catalyst is for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof. Other possible catalysts are the catalysts supported on carbon, catalysts based on antimony, catalysts based on aluminum (as $AlF_3$ and $Al_2O_3$ and oxyfluoride of alumina and aluminum fluoride). Generally speaking, catalysts that can be used are chromium oxyfluoride, aluminium fluoride and oxyfluoride, and supported or unsupported catalyst containing a metal such as Cr, Ni, Fe, Zn, Ti, V, Zr, Mo, Ge, Sn, Pb, Mg, Sb. Reference can also be made to the disclosures of WO-A-2007/079431, at page 7, lines 1-5 and 28-32, EP-A-939071, at paragraph [0022], WO2008/054781 at page 9 line 22 to page 10 line 34, WO2008/040969 in claim 1, all incorporated herein by reference.

Prior to its use, the catalyst is subjected to activation, typically with HF at high pressure, typically above about 10 bars (typically at a pressure above the pressure used in the gas-phase process), as described in U.S. Pat. No. 7,485,598, incorporated herein by reference. Any suitable conditions would also be appropriate.

A preferred embodiment uses a particular catalyst, which is a mixed catalyst, containing both chromium and nickel. The molar ratio Cr:Ni, with respect to the metallic element is generally between 0.5 and 5, for example between 0.7 and 2, including close to 1. The catalyst may contain in weight from 0.5 to 20% chromium and 0.5 to 20% nickel, preferably between 2 and 10% of each metal.

The metal may be present in metallic form or as derivatives, including oxide, halide or oxyhalide. These derivatives, including halide and halide oxides, are obtained by activation of the catalytic metal. Although the activation of the metal is not necessary, it is preferred.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process described below.

The catalyst may include chromium and nickel in a non-activated or activated form, on a support that has been subjected to activation or not.

Reference can be made to WO2009/118628, and especially to the disclosure of the catalyst from page 4, line 30 to page 7, line 16, which is incorporated herein by reference.

As is known in the art, an activation step can be performed, using fluorinated compounds, typically HF.

This step of the process of the present invention, as well as the entire process, is preferably run continuously.

The 1233xf fluorination process involves contacting 1233xf with HF in the reaction zone in a gas phase, under conditions sufficient to convert the 1233xf to fluorination products comprising, 1234yf and 245cb. Such conditions are given below. In addition, unreacted 1233xf and other co-produced underfluorinated intermediates which may be present in minor amounts are also recycled to the reactor.

The recycle stream contains the heavy fraction of the reaction stream which has been separated in the distillation step.

Typically, this step is carried out with a molar ratio HF:1233xf from 3:1 to 150:1, preferably 4:1 to 70:1, more preferably 5:1 to 50:1.

Typically, this step is carried out at a pressure from 1 to 20 bars, preferably 5 to 15 bars, more preferably 7 to 10 bars.

Typically, this step is carried out at a temperature of from 200 to 450° C., preferably from 300 to 430° C., more preferably from 320 to 420° C. The temperature of the bed can be substantially uniform in the reactor or can be adjusted along the path of the stream, decreasing or increasing along the direction of flow.

Contact times (catalyst volume divided by the total flow rate of reactants and co-feeds, adjusted to the operating pressure and temperature) are typically from 6 to 100 sec, preferably from 10 to 80 sec, more preferably from 15 to 50 sec.

An oxygen co-feed or chlorine co-feed can be used to extend the catalyst lifetime, typically in an amount of from 0.05 to 15 mole %, preferably 0.5 to 20 mole % of oxygen or chlorine per 1233xa. The oxygen can be introduced as an oxygen-containing gas such as air, pure oxygen, or an oxygen/nitrogen mixture. Chlorine can be introduced as a chlorine-containing gas such as pure chlorine, or a chlorine/nitrogen mixture.

The reactants can be fed to the reactor at the same location, at different locations, or using staged feeding at staged locations along the reactor. A preferred feeding system is to blow the gaseous reactants at the bottom of the reactor. Recycling can be done at the entry of the reactor or at an intermediate stage of the reactor; preferably at the entry of the reactor.

In another embodiment, the reaction stream exiting the gas-phase reactor can be recycled in part to the reactor, before it is subjected to the separation into a first, light, stream and a second, heavy stream. The recycling ratio can be as high as 0.7. This recycling allows dilution of 1233xf which is very reactive and avoids polymerisation.

Figure 2:
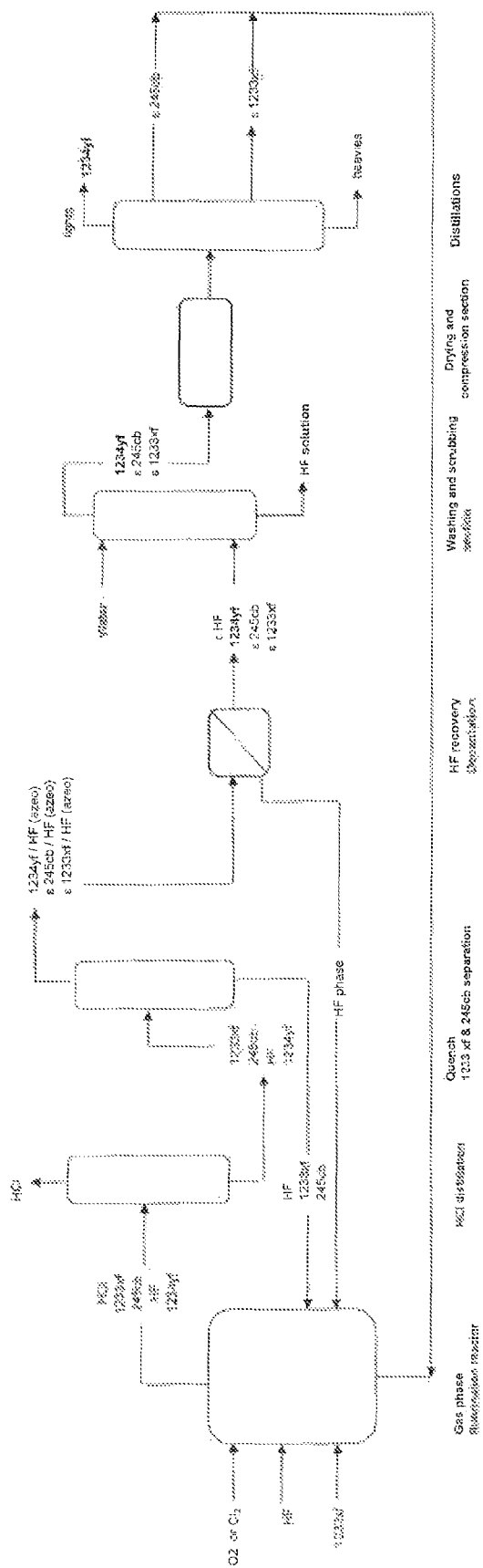
FIG. 2 is a schematic representation of a process implementing step (b)

This step can be carried out in an apparatus as depicted in FIG. 1 or 2.

FIG. 1 represents the process carried out in one embodiment of the invention. The gas-phase reactor is fed with 1233xf and HF. The reaction mixture exiting the reactor comprises HCl, unreacted 1233xf, unreacted HF, 1234yf, 245cb and a minor amount of 244bb. This reaction stream is separated by distillation into a first stream (light products) comprising HCl, 1234yf (possibly with a small amount of HF thereby forming an azeotropic mixture) and minor amounts of 245cb and 1233xf. A second, heavier, stream is obtained at the bottom of the distillation column, and comprises HF, 1233xf, 245cb and minor amounts of 244bb. The lighter fraction containing HCl, 1234yf (with HF) and minor amounts of other products is again distillated. The top flow comprises HCl, while the bottom flow comprises 1234yf and HF, which can again be separated using appropriate known methods. Among known methods is the decantation, which produces an HF rich flow which can be recycled to the gas-phase reactor. The streams exiting the decantation are treated according to known methods, including washing and scrubbing and distillations.

FIG. 2 represents another embodiment, where HCl is removed in a first step before distillation of the organic fluorinated products takes place. The gas-phase reactor is fed with 1233xf and HF. The reaction mixture exiting the reactor comprises HCl, unreacted 1233xf, unreacted HF, 1234yf, 245cb and a minor amount of 244bb. This reaction stream is separated by a first distillation into a stream containing mainly HCl and another stream containing the other products. This other stream is separated by distillation into a first stream (light products) comprising 1234yf (possibly with a small amount of HF thereby forming an azeotropic mixture) and minor amounts of 245cb and 1233xf. A second, heavier, stream is obtained at the bottom of the distillation column, and comprises HF, 1233xf, 245cb and minor amounts of 244bb. The lighter fraction containing 1234yf (with HF) and minor amounts of other products is obtained at the top of the second distillation tower. This top flow can again be separated using appropriate known methods. Among known methods is the decantation, which produces an HF rich flow which can be recycled to the gas-phase reactor. The streams exiting the decantation are treated according to known methods, including washing and scrubbing and distillations.

The pressure need not be the same in steps (a) and (b). Preferably the pressure in the second reactor is lower than the pressure in the first one so to gain in terms of pumps in the unit. The other process conditions need not be the same in steps (a) and (b) either.

Liquid-Phase Reaction of 240 into 1233xf.

The invention is based on the findings that 240db/240aa can be fluorinated in liquid phase into 1233xf, and that process conditions can be selected so as to achieve the reaction with a substantial selectivity into the desired product.

In a preferred embodiment, the liquid phase process is carried out in an organic phase. Using an organic phase rather than an HF phase favors the reaction into 1233xf. The prior art reported above disclose reaction mixtures comprising a substantial part of HF, hence an acidic phase. In an acidic phase, only saturated products are produced. The applicant has found that, surprisingly, there exist conditions that allow fluorination into 1233xf. Notably, when the reaction is carried out in an organic phase (comprised of the 240 starting material and/or solvent), then 1233xf can be formed. When HF is added to an initial medium, it will not remain in the medium since it reacts and the amount of HF (or concentration) will be very low, compared to the other products.

The term "organic phase" can thus be defined as referring to a reaction phase comprising the catalyst and the starting material and possibly a solvent if used, but substantially free of HF. Especially the process carried out in an "organic phase" refers to the process in which the initial load does not comprise any HF, in contrast with the prior art.

Because of particular operating conditions, gaseous 1233xf can be removed from the reactor under gaseous phase, keeping polymerization reactions at a low level.

The liquid phase fluorination of 240db/240aa into 1233xf is carried out in the presence of a catalyst.

The reaction can be implemented in a liquid solvent medium, the reaction zone being either loaded at the beginning with a starting amount of organic (the starting material) and/or the necessary quantity of solvent, or fed continuously with this quantity of solvent (possibly preliminary mixed with the raw material). When carried out with solvent, it is preferred that the solvent be loaded at the beginning; injections with a view of adjusting the quantity of solvent may however be carried out if necessary.

The reaction conditions (notably pressure) are such that the reactants are liquid. According to an embodiment the reactants are liquid while the reaction product is gaseous. The fact that the reaction products are gaseous allows their recovery in a gaseous phase at the exit of the reaction zone. The intermediate product, especially the 242 compound (trichlorodifluoropropane), is preferably liquid under the reaction conditions, even though it can be stripped away in the gaseous flow.

According to the invention, this stage is in particular implemented under a pressure higher than 2 bar. Advantageously, the pressure lies between 4 and 50 bar, in particular between 5 and 25 bar.

For example, the reaction may be implemented at a temperature ranging between 30° C. and 200° C., preferably between 40° C. and 170° C., advantageously between 50° C. and 150° C.

The molar ratio HF:starting compound lies generally between 0.5:1 and 50:1, preferably between 3:1 and 20:1. Values of about 5:1 can be used with advantage. The amount of HF added will correspond to the stoechiometry of the reaction (here 3), to which one will add the amount of HF that is present in the exiting streams (HF and organics) which are usually azeotropic mixtures.

The other reaction conditions, notably flow rates, can be determined by the skilled person according to common general knowledge, depending on the temperature, pressure, catalyst, reactant ratios, and the like. One shall take care that further fluorination reactions should be avoided so that 1233xf is the main product obtained (apart intermediate products).

The solvent, if used, is an inert organic solvent under the reaction conditions. Such a solvent will be generally saturated, advantageously in C2 to C6, in order to avoid the reactions of addition. Such solvents can for example be those mentioned in patent application FR2733227. Such solvents have a boiling point (measured at atmospheric pressure), for example higher than 40° C., advantageously higher than 50° C., in particular higher than 60° C. Higher reaction temperatures will imply higher pressures, so that the boiling point of the solvent under the conditions of reaction is higher than the temperature of implementation of the reaction.

One can in particular mention as a solvent the saturated compounds of ethane, propane or butane, substituted by at least two atoms of halogen, chosen among chlorine and fluorine, or a mixture thereof. As an example one can mention 1,2-dichloroethane, 1,2,3-trichloropropane, 1-chloro-1-fluoroethane, 1,1-difluoroethane, 1,1-dichloroethane and 1,3-dichloro-1-fluorobutane, tetrachlorofluoropropane isomers, trichlorodifluoropropane isomers and dichlorotrifluoropropane isomers, 1,1,1,3,3-pentafluorobutane and 1,1,2-trichloro-2,2-difluoroethane, or a mixture thereof. Nitrated solvents like nitromethane or nitrobenzene and sulfones like tetramethylene sulfone (also known as sulfolane) or dimethyl sulfone may also be used. A preferred solvent is the 1,1,2-trichloro-2,2-difluoroethane (F122). One can also use possibly reactive solvents, in so far as the product of their reaction is a nonreactive solvent. For example, one can also use the precursor of F122, namely F121 ($CCl_2F$—CHCl, 1,1,2-trichloro-2-fluoroethane) or perchloroethylene.

The solvent can be present in a quantity for a dilution ratio from at least 20%, preferably between 20% and 80%, advantageously between 40% and 60%.

The reaction is catalyzed. The catalysts may be catalysts known by the person skilled in the art of fluorinations in liquid phase.

One can use an acid of Lewis, a catalyst containing a metal halide, in particular containing halide of antimony, tin, tantalum, titanium, metals of transition such as molybdenum, niobium, iron halides, cesium, oxides of metals of transition, halides of metals of the IVb group, halides of metals of the Vb group, a fluorinated chromium halide, a fluorinated chromium oxide or a mixture of both. One can advantageously use metal chlorides and fluorides. Examples of such catalysts include: $SbCl_5$, $SbCl_3$, $TiCl_4$, $SnCl_4$, $TaCl_5$, $NbCl_5$, $TiCl_4$, $FeCl_3$, $MoCl_6$, $CsCl$, and their corresponding fluorinated derivatives. Pentavalent metal halides are suitable.

Advantageously one will use a catalyst containing an ionic liquid. These ionic liquids are particularly interesting for fluorination by HF in liquid phase. One will be able to mention the ionic liquids described in patent applications WO2008/149011 (in particular from page 4, line 1 to page 6 line 15, included by reference) and WO01/81353 in the name of the applicant, as well as the reference "liquid-phase HF Fluorination", Multiphase Homogeneous Catalysis, Ed. Wiley-VCH, (2002), 535.

One can operate with variable ratios catalyst/organic (including solvent if used), but in general one will prefer that this molar ratio lies between 2 mol % and 90 mol %, preferably between 4 mol % and 80 mol % and more preferably between 6 mol % and 75 mol %.

The starting material can be substantially pure 240db, and/or substantially pure 240aa, or it can be a mixture of the two. In one embodiment, the starting material is substantially pure 240db. In another embodiment, the starting material can be a typical 240db feed, i.e. one containing the 240aa isomer in an amount up to 40%, typically up to 20%.

A chlorine stream may be used to increase the lifetime of the catalyst, typically in a quantity from 0.05 to 20 mole %, preferably 0.5 to 15 mole % of chlorine per mole of starting compound 240db/240aa. Chlorine may be introduced pure or mixed with an inert gas such as nitrogen. The use of an ionic catalyst allows using small quantities of chlorine.

A raw material stabilizer may be used if necessary; typically in a quantity of 5-1000 ppm, preferably 10-500 ppm. This stabilizer is usually a polymerization inhibitor.

It is also possible that the product of the reaction be stripped using a light gas allowing its drive by mechanical entrainment. Removing gaseous 1233xf from the liquid phase reactor keep polymerization reactions at a low level (since polymerizable material is in a low amount in the medium) as well as side-reactions (such as addition onto the double bond of the 1233xf). The addition of a gaseous compound can be advantageous for the reaction, which can be favored for example by the improvement of agitation (bubbling).

This gas can be inert as the nitrogen or helium or the gas can be preferably HCl. When HCl is used, the reaction performs despite the addition into the medium of HCl, which is a reaction product.

Advantageously, this added gas is anhydrous hydrochloric acid. The flow of the stripping gas is determined according to the operating conditions. For example, the flow of HCl, compared to the flow of starting product is such that the molar ratio HCl:starting product lies between 0.5:1 and 5:1, advantageously, between 1:1 and 3:1.

The fluorination process in liquid phase according to the invention can be implemented continuously or semi-continuously. According to the preferred embodiment, the process is continuous.

The reactants (starting product and HF) and other compounds used in the reaction (chlorine, anhydrous HCl) can be fed in the reactor at the same place or at different places of the reactor. A preferred embodiment is when the gaseous compounds are injected in the bottom of the reactor, in particular in order to enhance the mechanical stripping and the mixing.

If a recycling is used, one can recycle directly at the inlet of the reactor or on a separate dip pipe.

Figure 4:
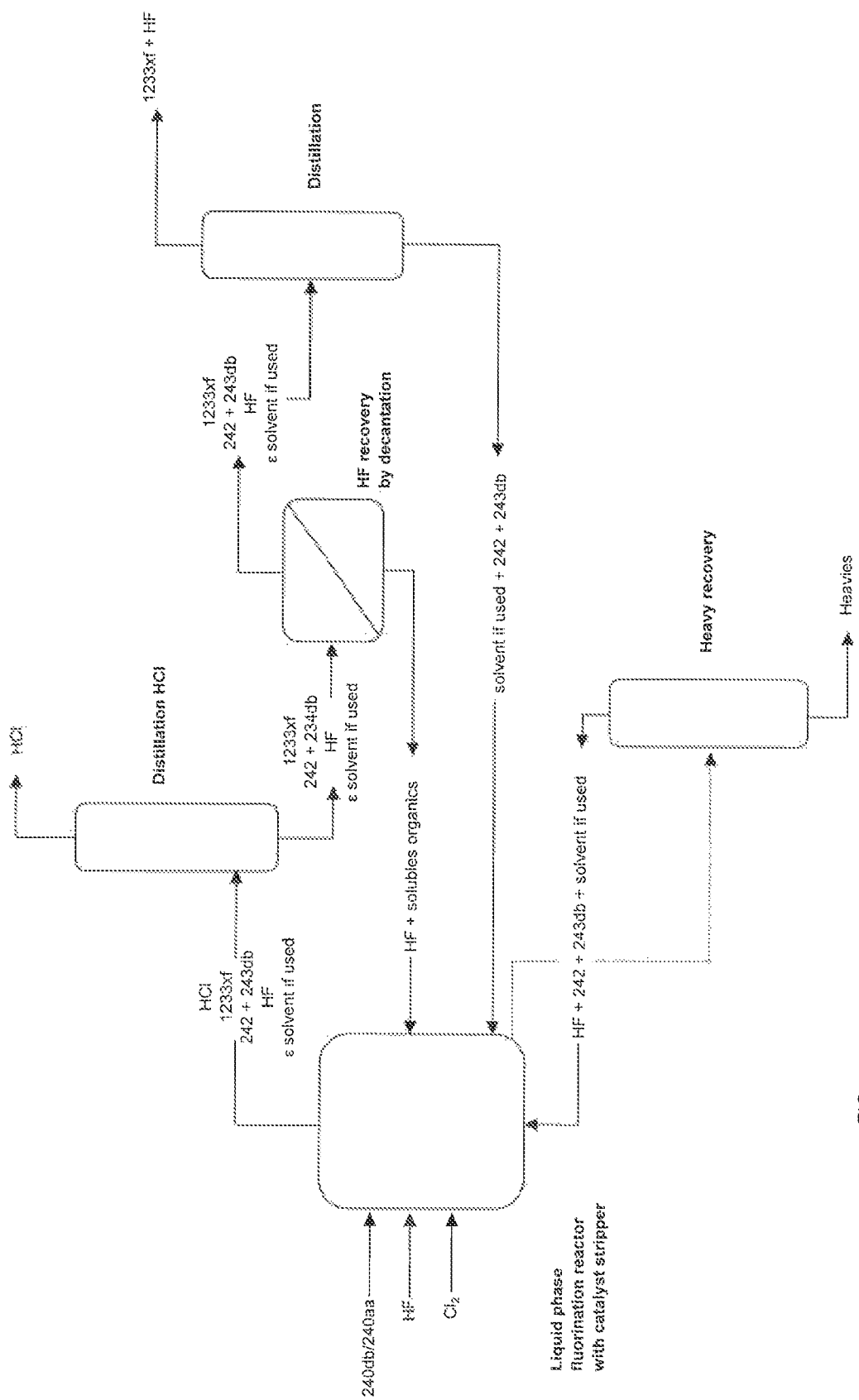
FIG. 4 is a schematic representation of a process implementing step (a) in liquid phase.

FIG. 4 is a schematic representation of a process according to an embodiment of the invention. The reactor (equipped with a catalyst stripping column, not shown in the figure) for the liquid phase reaction is loaded with catalyst, pentachloropropane and solvent if used. Then pentachloropropane and HF are supplied continuously. A stream of anhydrous HCl could also be injected.

The stream which is withdrawn from the reaction zone is in a gaseous form and mainly comprises 1233xf, HCl, HF as well as traces of stripped solvent 122 if any and other by-products including 242 isomers, and possibly 243 (dichlorotrifluoropropane) especially 243db (1,1,1-trifluoro-2,3-dichloropropane). This stream is introduced into a distillation column of HCl. At the top of the column is withdrawn a stream of HCl; at the bottom of the column a stream containing 1233xf, 242, HF as well as traces of 122 and 243db is withdrawn. Typically, this bottom stream will comprise between 30 mol % and 70 mol % of 1233xf, between 30 mol % and 70 mol % of HF as well as minor amounts, typically less than 10 mol %, preferably less than 5 mol %, of compounds of the series 242, 243 (especially 243db). This stream is sent towards a stage of separation by decantation. This decantation leads to two streams. The first stream comprises HF and soluble organics and solvent if any. This HF-rich stream is returned to the fluorination reaction. The second stream comprises 1233xf, 242, still a quantity of HF as well as traces of 122 and 243db. This stream is sent in a distillation column to be separated there. The traces of 122 and 243db are recovered at the bottom and are returned towards the fluorination reactor. The 242 product (and generally the higher saturated fluorinated products of the 240 series) will not build up, since it is an intermediate compound. A stream containing HF and 1233xf is withdrawn at the top. This top stream can be further separated or can be sent directly towards the next step. 242 isomers and/or 243db can be recycled in the process of the invention.

At the bottom of the liquid phase reactor a stream containing the heavies is withdrawn. It is believed, without wishing to be bound, that the heavies comprise oligomers of the $C_6F_6H_2Cl_2$ type. The bottom of the fluorination reactor is purged with a flow and a frequency such that the accumulation of heavies is avoided (rate of purging being defined by both a flow and frequency of purging as the skilled person can easily determine). This stream is treated in a column of recovery of the heavies. These heavies are eliminated at the bottom of this column. At the top of the column a stream containing HF, 122 and 242 isomers and 243db is recovered; this stream is recycled towards the fluorination reactor.

Gas-Phase Reaction of 240 into 1233xf.

The invention is based on the findings that 240db (and/or 240aa) can be catalytically fluorinated in gas phase into 1233xf. In one embodiment, the process conditions can be selected so as to achieve a reaction with an improved catalyst lifetime, when oxygen is cofed with 240.

The catalyst used in the invention is for example the same type of catalyst as used in step (b) disclosed above.

The present fluorination process involves contacting 240db with HF in the reaction zone in a gas phase, under conditions sufficient to convert the 240db to fluorination products comprising mainly 1233xf.

Typically, the process of the invention is carried out with a molar ratio HF:240 from 3:1 to 150:1, preferably 4:1 to 70:1, more preferably 5:1 to 50:1.

Typically, the process of the invention is carried out at a pressure from 1 to 20 bars, preferably 3 to 15 bars, more preferably 5 to 10 bars.

Typically, the process of the invention is carried out at a temperature of from 200 to 450° C., preferably from 300 to 430° C., more preferably from 320 to 420° C. The temperature of the bed can be substantially uniform in the reactor or can be adjusted along the path of the stream, decreasing or increasing along the direction of flow.

The temperature of this step (a) is usually less than the temperature of step (b), preferably by at least 30° C.

Contact times (catalyst volume divided by the total flow rate of reactants and co-feeds, adjusted to the operating pressure and temperature) are typically from 6 to 100 sec, preferably from 10 to 80 sec, more preferably from 15 to 50 sec.

An oxygen co-feed is used to extend the catalyst lifetime, typically in an amount of from 0.05 to 15 mole %, preferably 0.5 to 10 mole % of oxygen or chlorine per pentachloropropane molecule. The oxygen can be introduced as an oxygen-containing gas such as air, pure oxygen, or an oxygen/nitrogen mixture.

A chlorine cofed may also be used in lieu of the oxygen cofed (with the same operating conditions).

The reactants can be fed to the reactor at the same location, at different locations, or using staged feeding at staged locations along the reactor. A preferred feeding system is to blow the gaseous reactants at the bottom of the reactor. Recycling can be done at the entry of the reactor or at an intermediate stage of the reactor; preferably at the entry of the reactor. It is also possible to recycle part of the stream exiting the reactor.

A polymerization inhibitor can be used at any of the steps of the process to extend the catalyst life, typically in a concentration of from about 50-1000 ppm, more preferably between 100-500 ppm. The polymerization inhibitor can be p-methoxyphenol, t-amylphenol, limonene, d,l-limonene, quinones, hydroquinones, epoxides, amines and mixtures thereof. The preferred polymerization inhibitor is p-methoxyphenol or t-amylphenol. The co-feeding of a low level of a polymerization inhibitor can control such polymerization of chloroolefins and extend the life of the catalyst as described in U.S. Pat. No. 5,714,651, incorporated herein by reference.

The final and intermediate products are readily recovered by any means known in the art, such as by scrubbing, washing, extraction, decantation and preferably distillation. Any stream can also be further purified by distillation techniques.

Reactions are implemented in a dedicated reactor for reactions involving halogens. Such reactors are known to those skilled in the art and can include linings based eg Hastelloy®, Inconel®, Monel® or fluoropolymers. The reactor may also include means of heat exchange, if necessary.

As used herein, percentages are by molar percent unless specified otherwise.

The following examples illustrate the invention without limiting it.

EXAMPLES

Examples Directed to the Preparation of 1234yf Starting from 1233xf

In the following examples, use is made of a catalyst Ni—Cr/AlF$_3$ which is obtained as follows. The catalyst used is a mixed catalyst nickel/chromium of atomic ratio of Ni/Cr=1, supported on alumina fluoride and is prepared by impregnating solutions of nickel and chromic anhydride (CrO$_3$). After impregnation and drying, the solid is treated at a temperature between 320° C. and 390° C. in the presence of a mixture of hydrofluoric acid and nitrogen (concentration by volume of 5 to 10% of this acid in nitrogen). The catalyst bed is placed on a grid welded to the lower end of reactor. The reactor is equipped with a temperature measurement at three locations along the catalyst bed.

Example 1

Fluorination of 1233xf 150 ml of catalyst Ni—Cr/AlF$_3$ are introduced into the reactor. The reactor was fed with 16.4 g/hr of HF and 4.1 g/h 1233xf. The reaction temperature is 352° C. and atmospheric pressure. HF/1233xf molar ratio is 26.9 and the contact time of 4.9 seconds. The conversion rate is then 10.3%. The selectivities (amount of one product divided by the sum of all the products of reaction, this means without 1233xf) were 71.4% in 1234yf, 22.7% in 245cb. Other minor compounds detected are: 244bb, 1234ze and 245fa. (outlet gas flow contained 89.13 mol % 1233xf, 7.75 mol % 1234yf, 2.47 mol % 245cb and 0.65 mol % others).

Examples 2 to 6

The fluorination reaction of 1233xf is performed according to example 1 described above. The flows of HF and 1233xf are adjusted to obtain a molar ratio HF/1233xf close to 5 but varying contact time: 9.5, 18.8, 26.7, 37.9 and 39 seconds. The products that are mainly obtained are 1234yf and 245cb (if one excludes the 1233xf, not completely converted). The molar compositions 1234yf and 245cb are summarized in table 1.

|        | Contact time (s) | 1234yf (%) | 245cb (%) |
|--------|------------------|------------|-----------|
| Ex. 2  | 9.5              | 72.53      | 27.47     |
| Ex. 3  | 18.8             | 69.13      | 30.87     |
| Ex. 4  | 26.7             | 66.49      | 33.51     |
| Ex. 5  | 37.9             | 66.28      | 33.72     |
| Ex. 6  | 39               | 66.18      | 33.82     |

Example 7

The fluorination reaction of 1233xf is performed according to the embodiment described in Example 1 with an amount of 60 ml of catalyst introduced into the 60 ml reactor. The 245cb is added to the feed. The flow of 245cb is 2.1 g/hr, the flow 1233xf is 4.5 g/hr and the flow of HF is 16.2 g/hr. Hence, 100 mol of 1233xf are used with 47 mol 245cb. HF/1233xf molar ratio is equal to 24.5 and the contact time is equal to 4.8s. Air is continuously added in order to preserve the life of the catalyst. The amount of oxygen introduced is expressed in molar ratio $O_2/(1233xf+245cb)$ and is equal to 0.5%. The molar composition of gas leaving is analyzed by a gas chromatograph: 60.6% 1233xf, 26.6% 1234yf, 12.4% 245cb and some other impurities. (89.08 mol 1233xf; 39.07 mol 1234yf; 18.17 mol 245cb and 0.72 mol others).

Examples Directed to the Preparation of 1233xf Starting from 240 Via Liquid Route.

Figure 3:
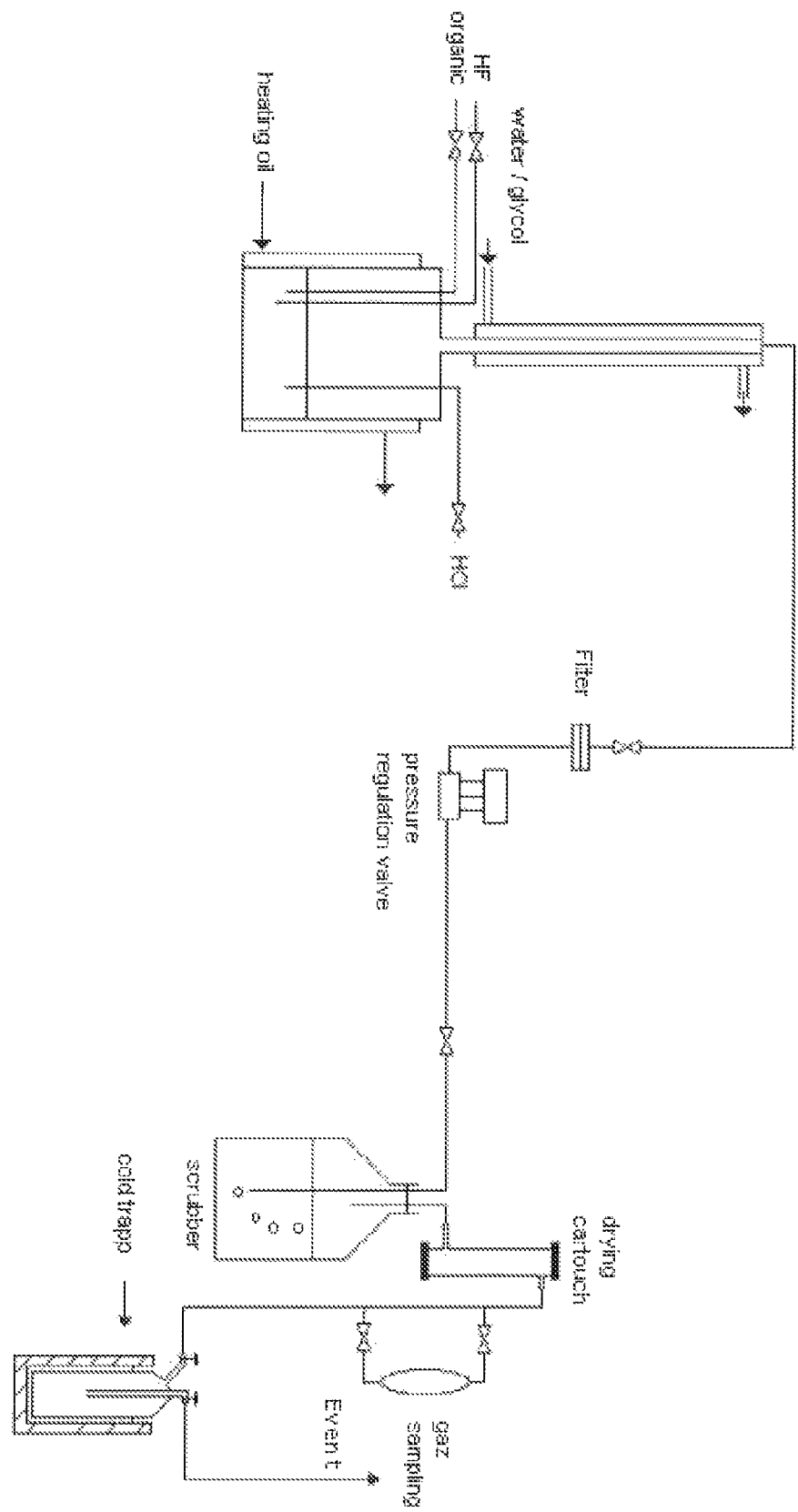
FIG. 3 is a representation of the experimental device used in the examples for the first step of the reaction in liquid phase.

Equipment used is described with reference to FIG. 3. It consists of a jacketed autoclave of a capacity of 1 liter, made of stainless steel 316L, which is stirred using a magnetic stirrer. It is equipped with pressure and temperature indicators. Apertures on the head of the autoclave allow the introduction of the reactants and degasification. It comprises at the top a condenser as well as a valve for regulating the pressure. The condenser is controlled in temperature using an independent thermostated bath.

The products of the reaction are extracted continuously during the reaction. They enter a scrubber which collects hydracids HF and HCl and then are cold trapped in liquid nitrogen. The increase of weight of the scrubber and of the trap makes it possible to establish a mass balance.

At the end of the period of reaction, the reaction medium is degassed in order to evacuate residual HF. For this period of degasification, the organics possibly drawn are also trapped, always after having crossed the scrubber which makes it possible to eliminate HF and HCl from the gas flow. In a last stage, the autoclave is opened and drained, a sample of the organic phase is analyzed after having hydrolyzed and extracted the catalyst with a hydrochloric acid solution.

The analysis is made then by gas phase chromatography on a sample of expanded liquid. The analysis by chromatography is carried out using a column CP Sil 8, dimensions 50 m*0.32 mm*5 μm. The programming of temperature of the furnace is the following one: 40° C. during 10 min then slope of 4° C./min until 200° C.

Considering that xi is the initial amount of moles of raw material and xf the total final amount of moles of raw material, conversion (%) is: (xi−xf)/xi*100. Selectivity of a product is calculated by the ratio between the amount of moles recovered of this product and the total amount of moles of products of reaction.

Examples 8 and 9

0.5 moles of 240db or 1,1,1,2,3-pentachloropropane and 0.2 moles of catalyst (0.2 moles of ethylmethylimidazolium chloride associated with 0.4 mole with $SbCl_5$, providing 0.2 moles of fluorinated complex catalyst emim$^+$Sb$_2$F$_{11}^-$emimcl) are introduced in the autoclave. In one case, 151 g of F122 or 1,1,2-trichloro-2,2-dichloroethane is added in the autoclave as solvent. HF is then added continuously with a constant flow of 1 mol/h during 5 hours. Temperature is 133° C. and absolute pressure is 9 bar. The set-point of the regulation of the condenser is always put at 90° C. In both cases, HCl was flowing through the autoclave to improve mixing and helping stripping out the products. The molar ratio HCl to 240db is near 2:1.

|                          | Example 8 | Example 9 |
|--------------------------|-----------|-----------|
| F122                     | —         | 151g      |
| Conversion               | 99.1%     | 99.7%     |
| Selectivity 1233xf (%)   | 19.4      | 54.2      |
| Selectivity 242 (%)      | 27.5      | 15.5      |
| Selectivity C6F6H2Cl2* (%) | 2.9     | 4.2       |
| others (%)               | 43.6      | 18.1      |
| Total mass balance       | 91.9 wt % | 91 wt %   |

*C6F6H2Cl2 structure identified by NMR as CF3—CCl=CH—CH=CCl—CF3

Hence, 1233xf can be produced in substantial amounts. This is obtained in a medium which is not an acidic medium but rather an organic medium.

Examples 10 and 11

The same apparatus as the examples above is used. 0.5 moles of raw material sample (240db or 240db with 10% of 240aa), 0.2 moles of catalyst (0.2 moles of ethylmethylimidazolium chloride associated with 0.4 mole with $SbCl_5$, or also represented as 0.2 moles of fluorinated complex catalyst emim$^+$Sb$_2$F$_{11}^-$emimcl) and 2 moles of F122 are introduced in the autoclave. HF is then added continuously with a constant flow of 1 mol/h during 5 hours. Temperature is 135° C. and absolute pressure is 9 bar. The set-point of the regulation of the condenser is always put at 90° C. For both cases, Helium was flowing through the autoclave to improve mixing and helping to carry out the products. The flow of helium is 5 l/h.

|                    | Example 10           | Example 11 |
|--------------------|----------------------|------------|
| Raw material       | 240db with 10% 240aa | Pure 240db |
| Conversion         | 97.6%                | 99.8%      |
| 143a (%)           | 0.03                 | 0.03       |
| 1233xf (%)         | 38.7                 | 43.7       |
| 1223xd (%)         | 1.2                  | 1.65       |
| 1232xf (%)         | 0.25                 | 0.22       |
| 243db (%)          | 1.37                 | 1.26       |
| 233ab (%)          | 0.65                 | 3.95       |
| C6F6H2Cl2* (%)     | 2.81                 | 2.77       |
| 242 (%)            | 34.5                 | 29.6       |
| C6H4F4Cl4 (%)      | 3.14                 | 2.79       |
| others (%)         | 15.43                | 14.1       |
| Total mass balance | 91 wt %              | 93 wt %    |

Examples Directed to the Preparation of 1233xf Starting from 240 Via Gas Route.

The equipment used, not shown, consists of a tubular reactor of an internal diameter of 19 mm, made of INCONEL® alloy 600 surrounded by a tubular oven. It is also equipped with pressure and temperature controller. The reactants, preliminarily vaporized thanks a heater, are introduced in gaseous phase at the top of the reactor.

At the outlet of the reactor, a sample of the products of the reaction is taken, washed by a pre-column and analyzed online by a gas phase chromatography equipped with low polarity capillary column.

The analysis by chromatography is carried out as above.

Example 12

Fluorination of 240db (1,1,1,2,3-pentachloropropane) is performed in the reactor described above with 79.4 cm³ of Ni—Cr catalyst supported on AlF$_3$.

The catalyst used is the same as in example 1.

The reactor was continuously fed with 15 g/hr of anhydrous HF and about 4.5 g/hr of 1,1,1,2,3-pentachloropropane at atmospheric pressure for 86 hrs. Thus, the contact time is 7.4 seconds, the molar ratio of HF to 240 is 36, and the reaction temperature is 340° C. The amount of oxygen is about 4 mol % with respect to the 240db. Results are given in the table 1.

Example 13

Fluorination of the mixture of 65.9% of 240db or 1,1,1,2,3-pentachloropropane and 34.9% of 240aa or 1,1,2,2,3-pentachloropropane is performed according to example 1 described above. The reactor was continuously fed with 16 g/hr of anhydrous HF and about 5.1 g/hr of 1,1,1,2,3-pentachloropropane at atmospheric pressure. Thus, the contact time is 6.9 seconds, the molar ratio is 34, and the reaction temperature is from 340° C. The amount of oxygen is about 4 mol % with respect to the total number of mole of 1,1,1,2,3-pentachloropropane and 1,1,2,2,3-pentachloropropane. Results are given in table 1.

Examples 14 and 15

Example 13 is repeated at different temperatures as indicated in table 1.

TABLE 1

| | | | Selectivity (Area (%)) | | |
| --- | --- | --- | --- | --- | --- |
| | Temp. °C. | Conversion % | 1234yf + 245cb | 1233xf | Others |
| Ex. 12 | 340 | 100% | 1.6 | 98.3 | 0 |
| Ex. 13 | 340 | 100% | 0.5 | 72.0 | 25.6 |
| Ex. 14 | 360 | 100% | 0.5 | 72.0 | 25.1 |
| Ex. 15 | 380 | 100% | 0.6 | 74.3 | 22.8 |

The invention claimed is:

1. Process for preparing 2,3,3,3-tetrafluoropropene, comprising the steps:
    (a) catalytic reaction of 1,1,1,2,3-pentachloropropane and/or 1,1,2,2,3-pentachloropropane with HF into 2-chloro-3,3,3-trifluoropropene; and
    (b) catalytic reaction of said 2-chloro-3,3,3-trifluoropropene into 2,3,3,3-tetrafluoropropene, wherein step (b) comprises:
        (i) contacting 2-chloro-3,3,3-trifluoro-1-propene with hydrogen fluoride in the gas phase in the presence of a fluorination catalyst under conditions sufficient to produce a reaction mixture;
        (ii) separating the reaction mixture into a first stream comprising HCl, 2,2,2,3-tetrafluoropropene and a second stream comprising HF, unreacted 2-chloro-3,3,3-trifluoro-1-propene and 1,1,1,2,2-pentafluoropropane; and
        (iii) recycling at least a part of the second stream back to step (i).

2. The process according to claim 1, wherein the first stream is separated into HCl and 2,2,2,3-tetrafluoropropene.

3. The process according to claim 1, wherein step (b) is carried out in the presence of a catalyst comprising Ni—Cr, preferably supported.

4. The process according to claim 3, wherein said catalyst is supported on a support selected from fluorinated alumina, fluorinated chromia, fluorinated activated carbon or graphite carbon.

5. The process according to claim 1, wherein step (a) is carried out in a liquid-phase.

6. The process according to claim 5, wherein step (a) is carried out in an organic medium.

7. The process according to claim 6, carried out in a solvent.

8. The process according to claim 7, in which the solvent is selected from 1,2-dichloroethane, 1,2,3-trichloropropane, 1-chloro-1-fluoroethane, 1,1-difluoroethane, 1,1-dichloroethane, 1,3-dichloro-1-fluorobutane, tetrachlorofluoropropane isomers, trichlorodifluoropropane isomers, dichlorotrifluoropropane isomers, 1,1,1,3,3-pentafluorobutane, 1,1,2-trichloro-2,2-difluoroethane, nitrated solvents, 1,1,2-trichloro-2-fluoroethane, perchloroethylene, or mixtures thereof.

9. The process according to claim 5 in which the catalyst is an ionic liquid.

10. The process according to claim 5, in which the 2-chloro-3,3,3-trifluoropropene is withdrawn in the gaseous state.

11. The process according to claim 5, comprising:
    contacting 1,1,1,2,3-pentachloropropane or/and 1,1,2,2,3-pentachloropropane with hydrogen fluoride in a liquid phase in an organic medium under conditions sufficient to form a reaction mixture comprising 2-chloro-3,3,3-trifluoropropene;
    separating the reaction mixture into a first stream comprising HCl, and a second stream comprising HF and 2-chloro-3,3,3-trifluoropropene.

12. The process according to claim 1, wherein step (a) is carried out in a gas-phase.

13. The process according to claim 12, carried out in the presence of oxygen.

14. The process according to claim 12, wherein step (a) is carried out in the presence of a catalyst comprising Ni—Cr, preferably supported.

15. The process according to claim 12, wherein said catalyst is supported on a support selected from fluorinated alumina, fluorinated chromia, fluorinated activated carbon or graphite carbon.

16. The process according to claim 12, wherein the temperature in step (b) is higher than the temperature of step (a) by at least 30° C.

17. The process according to claim 1, in which said 1,1,1,2,3-pentachloropropane contains up to 40 mol % of 1,1,2,2,3-pentachloropropane.

18. The process according to claim 1 which is continuous.

19. The process according to claim 2, wherein the separation into HCl and 2,2,2,3-tetrafluoropropene comprises a distillation step.

20. The process of claim 8 wherein said nitrated solvent is selected from nitromethane and nitrobenzene.

21. The process of claim 8 wherein said sulfone is selected from tetramethylene sulfone and dimethyl sulfone.

* * * * *

UNITED STATES PATENT AND TRADEMARK OFFICE
CERTIFICATE OF CORRECTION

PATENT NO. : 9,120,716 B2  
APPLICATION NO. : 13/879435  
DATED : September 1, 2015  
INVENTOR(S) : Wendlinger et al.

Page 1 of 1

It is certified that error appears in the above-identified patent and that said Letters Patent is hereby corrected as shown below:

On the title page of the patent:

(75) Inventors: "Philippe Bonnet, Lyons (FR)" should be --Philippe Bonnet, Lyon (FR)--; "Nicolas Doucet, Lyons (FR)" should be --Nicolas Doucet, Lyon (FR)--.

Signed and Sealed this  
Eighth Day of March, 2016

Michelle K. Lee  
*Director of the United States Patent and Trademark Office*